United States Patent
Kim

(12) 
(10) Patent No.: US 6,548,060 B1
(45) Date of Patent: Apr. 15, 2003

(54) ANTI-APOPTOTIC USE OF HUMAN GLUTAMINYL-TRNA SYNTHETASE WITH TWO CONSECUTIVE PRO-APOPTOTIC MEDIATORS

(76) Inventor: Sunghoon Kim, 103-1107 Yeoksamlukcy APT, Dogok-Dong, Kangnam-Ku, Seoul (KR)

( * ) Notice: Subject to any disclaimer, the term of this patent is extended or adjusted under 35 U.S.C. 154(b) by 0 days.

(21) Appl. No.: 09/442,630

(22) Filed: Nov. 18, 1999

(51) Int. Cl.$^7$ .................. A61K 38/53; A61K 31/713; C12N 15/54
(52) U.S. Cl. .................. 424/94.5; 514/2; 514/12; 514/44; 435/183; 435/194
(58) Field of Search ................... 435/183, 194; 530/350; 424/94.5; 514/44, 2, 12

(56) References Cited

U.S. PATENT DOCUMENTS 6,159,731 A * 12/2000 Yang et al. .................. 435/235

OTHER PUBLICATIONS

Shiba, et al., *Maintaining genetic code through adaptations of tRNA synthetases to taxonomic domains*, Trends Biochem. Sci, 1997, 22:453–457.

Marc Mirande, *Aminoacyl–tRNA Synthetase Family from Prokaryotes and Eukaryotes: Structural Domains and Their Implications*, Prog. Nucleic Acid Res. Mol. Biol., 1991, 40:95–142.

Kisselev & Wolfson, *Aminoacyl–tRNA Synthetases form Higher Eukaryotes*, Prog. Nucleic Acid Res. Mol. Biol., 1994, 48:83–142.

David Yang, *Mammalian Aminoacyl–tRNA Synthetases*, Current Topics in Cellular Regulation, 1996, 34:101–136.

Wakasugi & Schimmel, *Two Distinct Cytokines Released from a Human Aminoacyl–tRNA Synthetase*, Science, 1999, 248:147–151.

Park et al., *Precursor of Pro–apoptotic Cytokine Modulates Aminoacylation Activity of tRNA Synthetase*, J. Biol. Chem., 1999, 274(24):16673–16676.

Knies et al., *Regulation of endothelial monocyte–activating polypeptide II release by apoptosis*, Proc. Natl. Acad. Sci. USA, 1998, 95:12322–12327.

Rho et al., *Genetic dissection of protein–protein interactions in multi–tRNA synthetase complex*, Proc. Natl. Acad. Sci. USA, 1999, 96:4488–4493.

Gyuris et al., *Cdi1, a Human G1 and S Phase Protein Phosphatase That Associates with Cdk2*, Cell, 1993, 75:791–803.

Yang et al., *Daxx, a Novel Fas–Binding Protein That Activates JNK and Apoptosis*, Cell, 1997, 89:1067–1076.

Chang et al., *Activation of Apoptosis Signal–Regulating Kinase 1 (ASK1) by the Adapter Protein Daxx*, Science, 1998, 281:1860–1863.

Ichijo et al., *Induction of Apoptosis by ASK1, a Mammalian MAPKKK That Activates SAPK/JNK and p38 Signaling Pathways*, Science, 1997, 275:90–94.

Saitoh et al., *Mammalian thioredoxin is a direct inhibitor of apoptosis signal–regulating kinase (ASK) 1*, The Embo J., 1998, 17(9):2596–2606.

Hollenbach, et al., *The Pax3–FKHR oncoprotein is unresponsive to the Pax3–associated repressor hDaxx*, The Embo J., 1999, 18(13): 3702–3711.

Pluta, et al., *Interphase–specific association of intrinsic centromere protein CENP–C with HDaxx, a death domain–binding protein implicated in FAS–mediated cell death*, J. Cell. Sci., 1998, 111:2029–2041.

Roh et al., *A Multifunctional Repeated Motif Is Present in Human Bifunctional tRNA Synthetase*, J.. Biol. Chem., 1998, 273(18): 11267–11273.

* cited by examiner

Primary Examiner—Gabrielle Bugaisky
(74) Attorney, Agent, or Firm—Foley & Lardner

(57) ABSTRACT

Aminoacyl-tRNA synthetases are the enzymes catalyzing ligation of their cognate amino acids and tRNAs. Human glutaminyl-tRNA synthetase (QRS) consists of the unique N-terminal extension (236 aa) and the C-terminal catalytic domain (539 aa). Here, we found that the N- and C-domains of QRS interacted with pro-apoptotic mediator, Daxx, and its downstream kinase, ASK1 (apoptosis signal-regulating kinase), respectively. The experimental results suggest that QRS may inhibit the ASK1 activity via two different ways. First, its C-terminal domain made direct inhibitory interaction with ASK1. Second, it inhibited the pro-apoptotic interaction between Daxx and ASK1. QRS also blocked the Daxx-ASK1 mediated apoptosis. Thus, QRS is not only an enzyme for protein synthesis but also plays a regulatory role in apoptosis

4 Claims, 6 Drawing Sheets

SEQUENCE LISTING

<160> NUMBER OF SEQ ID NOS: 6

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 1
ccggaattcc ggatggccac cgctaacagc                                    30

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 2
ccgctcgagc ggctaatcag agtctgagag c                                  31

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 3
ccgctcgaga tgaactacaa gaccccaggc t                                  31

```
<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 4
atttgcggcc gctctagaac tagt                                      24

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 5
aatgaattca tggcggctct agactcc                                   27

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 6
ccggtcgact cactcaccag gcttgtggaa                                30
```

ANTI-APOPTOTIC USE OF HUMAN GLUTAMINYL-TRNA SYNTHETASE WITH TWO CONSECUTIVE PRO-APOPTOTIC MEDIATORS

FIELD OF THE INVENTION

This invention relates to novel anti-apoptotic use of human glutaminyl-tRNA synthetase with two consecutive pro-apoptotic mediators, that are ASK1 and Daxx.

BACKGROUND OF THE INVENTION

Apoptosis is a normal physiologic process that leads to individual cell death. This process of programmed cell death is involved in a variety of normal and pathogenic biological events and can be induced by a number of unrelated stimuli. Changes in the biological regulation of apoptosis also occur and diseases related to aging. Recent studies of apoptosis have implied that a common metabolic pathway leading to cell death may be initiated by a wide variety of signals, including hormones, serum growth factor deprivation, chemotherapeutic agents, ionizing radiation and infection by human immunodeficiency virus(HIV).

While apoptosis is a normal cellular event, it can also be induced by pathological conditions and a variety of injuries. Apoptosis is involved in a wide variety of conditions including but not limited to, cardiovascular disease, cancer regression, immunoregulation, viral diseases, anemia, neurological disorders, gastrointestinal disorders, including but not limited to, diarrhea and dysentery, diabetes, hair loss, rejection of organ trnasplants, prostate hypertrophy, obesity, ocular disorders, stress and aging.

Aminoacyl-tRNA synthetases (ARSs) play an essential role in protein synthesis, decoding genetic information into amino acids. These enzymes were generated early in evolution and accumulated a wide range of structural and functional diversity. The structural difference is not only observed between different ARSs but also between the same ARSs of different phylogenetic kingdoms (1). ARSs of higher eukaryotes have adopted many peculiar features in their structure and behavior distinguishable from those of prokaryotes (2–4).

For instance, some ARSs are functionally linked to apoptosis. Human tyrosyl-tRNA synthetase is released from the cell upon apoptosis and split into two distinct pro-apoptotic cytokines (5). The precursor of pro-apoptotic cytokine, EMAPII (endothelial monocyte activating polypeptide II) is associated with the N-terminal non-catalytic extension of arginyl-tRNA synthetase to facilitate aminoacylation (6). The C-terminal cytokine domain of this precursor is released by an apoptotic signal and exerts its pro-apoptotic function (7).

SUMMARY OF THE INVENTION

Aminoacyl-tRNA synthetases are the enzymes catalyzing ligation of their cognate amino acids and tRNAs. Human glutaminyl-tRNA synthetase (QRS) consists of the unique N-terminal extension (236 aa) and the C-terminal catalytic domain (539 aa). Here, we found that the N- and C-domains of QRS interacted with pro-apoptotic mediator, Daxx, and its downstream kinase, ASK1 (apoptosis signal-regulating kinase), respectively. The experimental results suggest that QRS may inhibit the ASK1 activity via two different ways. First, its C-terminal domain made direct inhibitory interaction with ASK1. Second, it inhibited the pro-apoptotic interaction between Daxx and ASK1. QRS also blocked the Daxx-ASK1 mediated apoptosis. Thus, QRS plays a regulatory role in apoptosis and thus can be used to control cell death.

BRIEF DESCRIPTION OF THE DRAWINGS

FIG. 5. The effect of QRS on the ASK1 activity A. HA-ASK1 (4 ug) co-expressed in 293 cells with QRS-F, -N or -C (as in: FIG. 3) was precipitated with anti-HA antibody and the immunocomplex kinase activity of ASK1 was assayed using 1 uCi [$\gamma$-$^{32}$P] ATP and 2 ug of MBP (Sigma) as an exogenous substrate (13). Phosphorylation of MBP was visualized by autoradiography B. pcDNA-Flag-ASK1 (1 g) was transfected into 293 cells in 60 mm dishes with pcDNA3-Daxx-CA (the constitutive active mutant of Daxx, C-terminal 242 aa) (2 ug) and pcDNA3-QRS (1 ug). Total amounts of the transfected DNA were adjusted with pcDNA3. The ASK1 activity was measured as above using GST-SEK1 as a substrate (12).

DETAILED DESCRIPTION OF THE INVENTION

Figure 1:
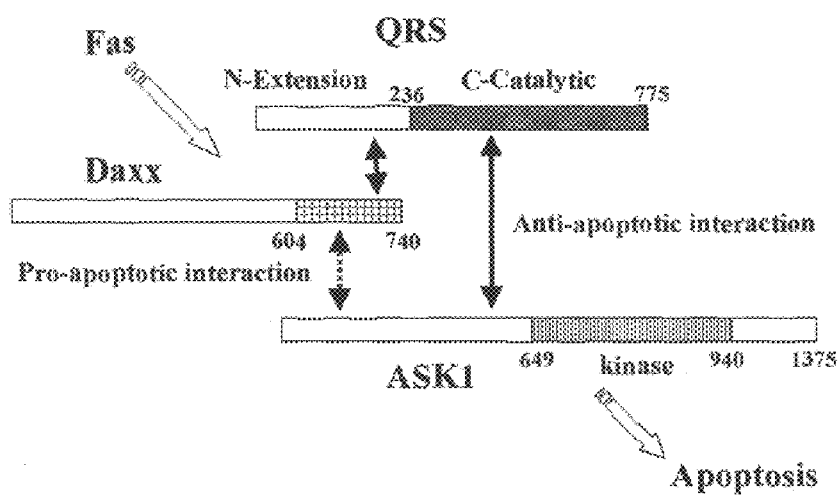
FIG. 1. Structural arrangement of human QRS and its interacting apoptotic mediators, Daxx and ASK1. Human QRS consists of the unique N-terminal extension and C-terminal catalytic domains (8). Daxx is a pro-apoptotic mediator associating with Fas via its C-terminal region (10) and then activates its downstream kinase ASK1 (11) via its interaction with the N-terminal domain of ASK1 (dotted line). From the following experiments, the N- and C-terminal domains of QRS were determined to interact Daxx and ASK1, respectively. The drawing simply shows the interaction relationship of the three molecules and does not necessarily reflect cellular locations of these molecules.

In the present work, we found that human QRS also modulates apoptotic process. Human QRS contains 775 amino acids (FIG. 1), consisting of the N-terminal extension and C-terminal catalytic domains. We previously reported that its N-terminal 236 amino acid extension is involved in the interactions with other ARSs within the multi-ARS complex (8). Although the N-terminal extension of RRS is associated with other ARSs, it also interacts with pro-EMAPII (6). We thus searched for the cellular molecules interacting with the N-terminal extension of QRS using yeast two hybrid system (9). From the screening of about 500,000 clones of human fetal brain cDNA library (Invitrogen), four positive clones encoding different C-terminal parts of human Daxx were isolated (data not shown). The smallest clone among them was the C-terminal 137 aa polypeptide. (FIG. 1, Daxx-C), indicating that this part would interact with the N-terminal extension of QRS.

Figure 2:
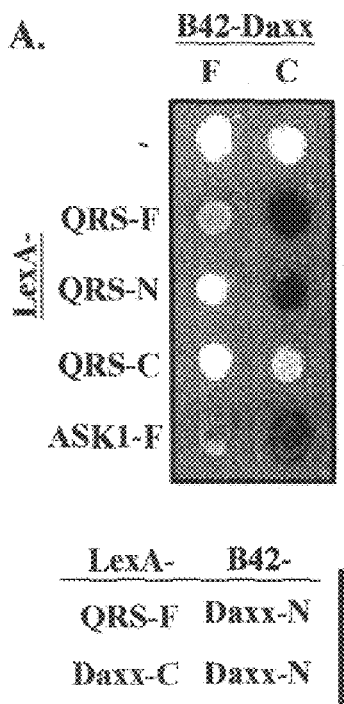
FIG. 2. Interaction of QRS-N and Daxx-C. A. (upper panel) The interaction of QRS and Daxx was mapped by yeast two hybrid analysis. The full-length (F), N-terminal 236 aa (N) and C-terminal 539 aa (C) peptides of QRS, and the full-length ASK1 were fused to LexA (DNA-binding protein). The full-length (F) and C-terminal 137 aa peptide (C) of human Daxx were fused to B42 (transcription activator). The pairs of LexA and B42 hybrid proteins were expressed in a yeast tester strain and the positive interactions were determined by the formation of blue colonies as described previously (8). (lower panel) The interaction between the N-terminal 610 aa and C-terminal 137 aa peptides of Daxx was tested as described above B. The interaction between Daxx-C and QRS-N was tested by in vitro pull down method as described previously with slight modifications (16). Daxx-C and QRS-N were expressed as His (pET28a, Novagen) and GST (pGEX4T-2, Amersham Pharmacia Biotech) fusion proteins, respectively and purified following the manufacturer's instructions. The purified His-Daxx-C (5 ug) was mixed with GST or GST-QRS-N (5 ug) at 4° C. for 30 min in 20 mM sodium phosphate buffer, pH 7.8, containing 500 mM NaCl. The GST proteins were precipitated with the GST resin (10 ul) and the precipitated proteins were eluted and resolved by 12% SDS-polyacrylamide gel electrophoresis and stained with Coomasie blue.
Figure 2:
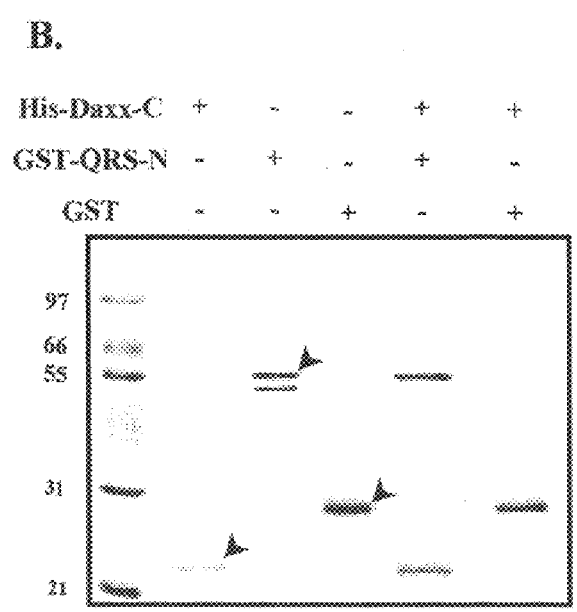

Human Daxx was originally identified to be associated to Fas to mediate apoptotic signal ( 10) to its downstream kinase, ASK1 (11). The activation of ASK1 then results in activation of Jun N-terminal kinase (JNK) and p38 for cellular apoptosis (12). The interaction between QRS and Daxx was further refined by yeast two hybrid analysis. The full-length, N- and C-domains of QRS were tested for the interaction with Daxx-F and -C. Daxx-C interacted with QRS-F and -N but very weakly with QRS-C (FIG. 2A. upper panel). Interestingly, the interaction of Daxx-F with QRS was weaker than that of Daxx-C, suggesting that the C-terminal region of Daxx may be masked somehow by its N-domain. We thus tested whether the N- and C-domains of Daxx interact with each other. As expected, Daxx-N interacted with its own C-domain but not with QRS, supporting this possibility (FIG. 2A, lower panel). Daxx-C also showed the interaction with ASK1, suggesting that this region contains residues interacting with ASK1.

The interaction between the Daxx-C and QRS-N was confirmed by in vitro pull down experiment. Daxx-C and QRS-N were expressed as His and GST fusion proteins, respectively. The purified two fusion proteins were then mixed and precipitated with the GST resin. Daxx-C was co-precipitated with QRS-N, confirming the direct interaction between the two molecules (FIG. 2B).

Figure 3:
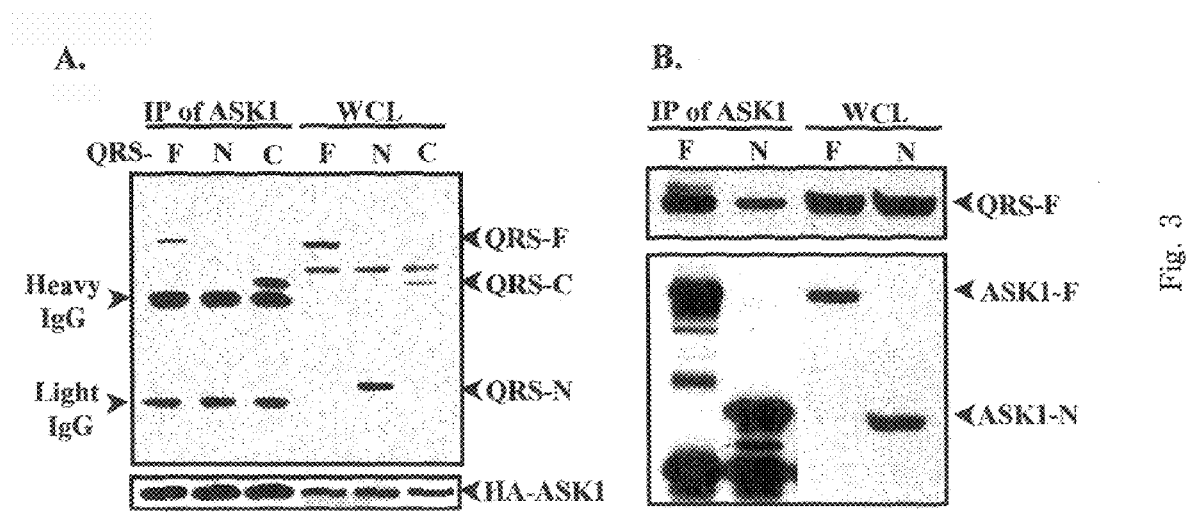
FIG. 3. Interaction of QRS-C and ASK1-N. A. The cDNA (4 ug each) encoding QRS-F. -N or -C (Myc tagged) cloned in pcDNA3 was transfected into 293 cells in 100-mm dishes with 0.5 ug pcDNA3-HA-ASK1 (a kind gift of Dr. Ichijo, Tokyo university, Japan). Co-immunoprecipitation between HA-ASK1 and QRS was carried out as described previously (11) using anti-HA antibody (Santa Cruz). The precipitated proteins were resolved in 10% SDS-polyacrylamide gel, and the presence of QRS-F and -N, and -C were detected by immunoblotting with anti-QRS (17) and Myc (9E10, Boehringer Mannheim) antibodies, respectively. -B. pcDNA3-QRS-F (4 ug) was co-transfected into 293 cells with pcDNA3-HA-ASK1-F (full length) or -N (N-terminal 649 aa) (4 ug each). The cells were harvested after 24 hrs and the ASK1 peptides were precipitated with anti-HA antibody and co-precipitation of QRS was determined by immunoblotting with anti-QRS antibody. Expression of the indicated proteins was confirmed by immunoblotting of whole cell lysate (WCL) with their respective antibodies.

Since ASK1 is the immediate downstream kinase of Daxx, we tested whether QRS also interacts with ASK1. The interaction of the two proteins was determined by co-immunoprecipitation. Each of QRS-F, -N and -C was co-expressed with HA-tagged ASK1 in 293 cells. After confirming expression of these proteins (FIG. 3A, WCL), HA-ASK1 was precipitated with anti-HA antibody. QRS-F and -C, but not -N, were co-precipitated with HA-ASK1 (FIG. 3A). The interaction of QRS-C and ASK1 was also confirmed by in vitro pull down assay (data not shown). Since the N-terminal 649 aa peptide was previously determined to be a regulatory domain interacting with Daxx, (FIG. 1), we tested whether QRS interacts with ASK1-N or -C. QRS was precipitated with ASK1-F and -N although the interaction with ASK1-N was weaker than that with ASK1-F (FIG. 3B). However, we could not test whether QRS also interacted with ASK1-C for its instability (data not shown).

Although the interaction of QRS with Daxx was shown by genetic and in vitro pull down assays (FIG. 2A and B), Daxx was not co-immunoprecipitated with QRS while it was with ASK1 (FIG. 4A). These results suggest that Daxx and QRS may be differently compartmentalized or do not associate in the cell. We thus tested whether the cellular interaction between the two molecules depends on the expression of ASK 1. When the three proteins were co-expressed, QRS was co-precipitated with Daxx (FIG. 4A). However, the interaction of ASK1 with Daxx was decreased by QRS, indicating the competition of QRS with ASK1 for the binding to Daxx. Expression of the three proteins was confirmed in whole cell lysate (FIG. 4B).

The direct interaction of QRS with ASK1 (FIG. 3), and its inhibition of the interaction between ASK1 and Daxx (FIG. 4) suggest that QRS may inhibit the ASK1 activity. To test this possibility, QRS-F, -N and -C were expressed in 293 cells with HA-ASK1. The kinase activity of ASK1 was measured using myelin basic protein (MBP) as an exogenous substrate (13). The ASK1 activity was inhibited by the expression of QRS-F and -C but not of QRS -N (FIG. 4A), indicating the direct inhibitory effect of QRS-C on the ASK1 activity. We then tested whether QRS can block the Daxx-induced ASK1 activity. For the experiment, we used the C-terminal 242 aa peptide of Daxx (Daxx-CA) that constitutively activates ASK1 (11) and GST-SEK1 (12) as a reaction substrate. The active mutant of Daxx (Daxx-CA) activated ASK1 but QRS inhibited the ASK1 activity enhanced by Daxx (FIG. 5B).

Figure 6:
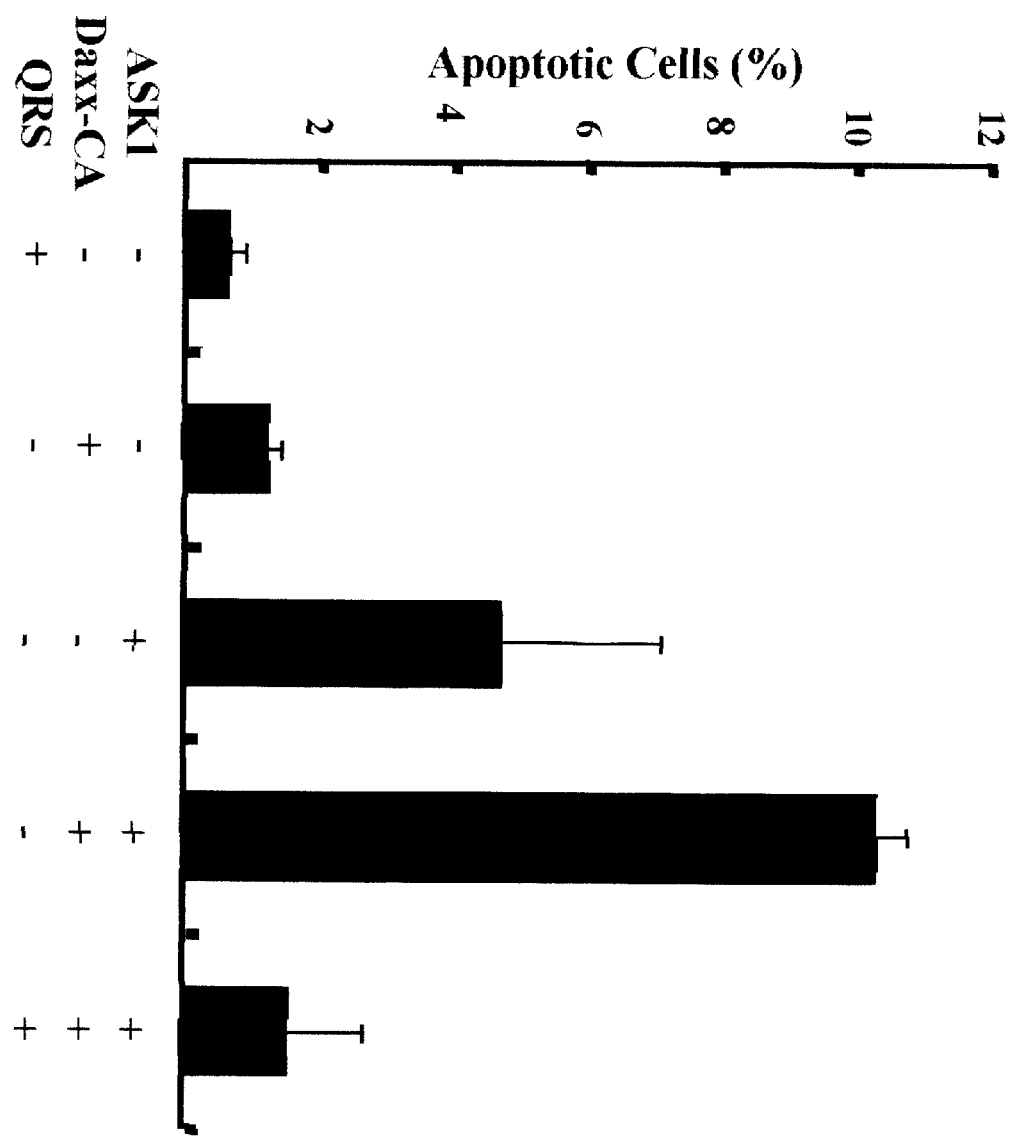
FIG. 6. The effect of QRS on the Daxx-ASK1 induced apoptosis. HeLa cells precultured in 6-well plates for 2 days were transfected with pcDNA3-QRS (2 ug), -Daxx-CA (1.5 ug) and -ASK1 (0.5 ug). In every transfection, pCMV-$\beta$-gal (Stratagene) (1 g) containing $\beta$-galactosidase gene was co-transfected. Total amounts of the transfected DNA were adjusted to be the same with pcDNA3. The cells were fixed with 0.2% glutaraldehyde and 2% formaldehyde following 24 hrs after transfection, and then stained with 5-bromo-4-chloro-3-indolyl $\beta$-D-galactoside for 3–5 hrs and the cells undergoing apoptosis were counted. The dead cells were determined by apoptotic morphology (10). At least 500 $\beta$-galactosidase positive cells were scored for each transfection in triplicate and the mean percentages of apoptotic blue cells and their standard errors were determined.

The activation of ASK1 triggers its downstream apoptotic cascades (12). Since QRS inhibited the activity of ASK1, it is expected to block apoptosis mediated by ASK1. We tested this possibility by expressing these molecules in HeLa cells (FIG. 6). Each of QRS, Daxx-CA or ASK1 alone did not induce a significant apoptosis. Co-expression of ASK1 and Daxx-CA then enhanced apoptotic cells to almost 11%. Additional expression of QRS then decreased the apoptic cells to below than 2%, suggesting that QRS blocks the Daxx-ASK1 induced apoptosis.

Figure 4:
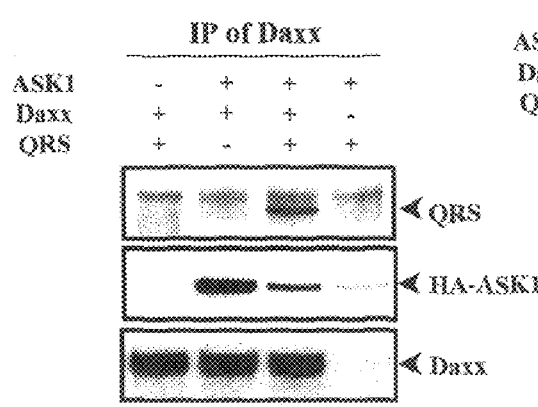
FIG. 4. Co-immunoprecipitation of QRS and Daxx. A. Combinations of pcDNA3-ASK1, -Daxx and -QRS (each 4 ug) were transfected into 293 cells cultured in 100 mm dishes. Total amounts of the DNAs used for transfection were adjusted to be the same with pcDNA3. Co-immunoprecipitation was carried out with anti-Daxx rabbit antibody (Santa Cruz). The precipitated proteins were resolved by 8% gel electrophoresis, and QRS, ASK1 and Daxx were detected with anti-QRS, anti-HA and anti-Daxx goat (Santa Cruz) antibodies, respectively B. Expression of the three proteins was confirmed by immunoblottting of these proteins in whole cell lysate.
Figure 4:
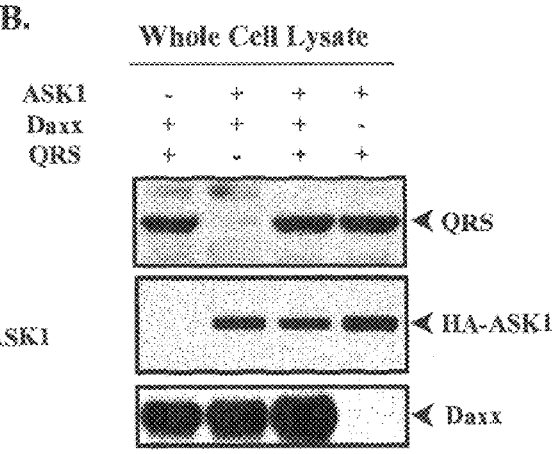
Figure 5:
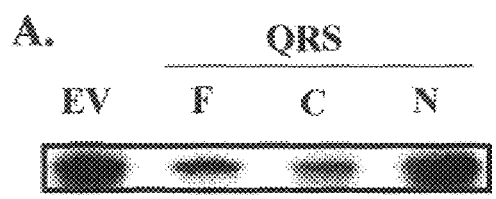
Figure 5:
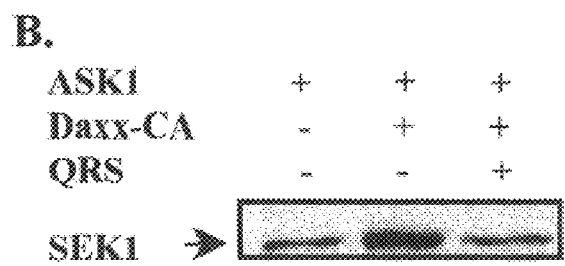

The cellular interaction of Daxx and QRS was dependent on ASK1 although QRS and ASK1 competed for the Daxx binding (FIG. 4). These results can be explained by a couple of different models. First, ASK1 may change the cellular distribution of Daxx. Although Daxx was first reported to be associated with Fas embedded in cellular membrane, the following reports suggested that it is localized in nucleus interacting with different nuclear factors (14, 15). If this is the case, QRS in cytoplasm would not meet Daxx in nucleus unless one protein is translocated to other compartment. Daxx may be localized in cytosol for the pro-apoptotic interaction with ASK1, and QRS may inhibit the formation of this complex. Second, the conformation of Daxx may be changed by the interaction with ASK1 to open its C-terminal domain that has a higher affinity to QRS. Then, QRS may attack this complex to block the activity of ASK 1. In this sense, it is worth noting that ASK1 bound to the full-length Daxx better than QRS whereas the opposite was the case for the interaction with Daxx-C (FIG. 2A). Understanding regulatory and molecular mechanisms for the interactions between these three molecules await further investigation.

The relationship of ARSs to apoptosis has been previously reported in the cases of human tyrosyl- and arginyl-tRNA synthetases. The former contained the pro-apoptotic cytokine domains within its structure while the latter harbors the precursor of cytokine. Here, we report that human QRS could repress apoptosis via bipartite interactions with two consecutive pro-apoptotic molecules, Daxx and ASK1 (FIG. 1). These reports suggest that ARSs play a pivotal role between cell proliferation and death, not only as a catalysis but also as a regulator.

EXAMPLE 1

Preparation of QRS Antibody

The DNA fragment encoding the N-terminal 236 aa of human QRS was isolated from pLexA vector [Rho, 1999 #6878] and subcloned into pET28a (Novagen). The His-QRS-N was expressed in *E. Coli* BL21 (DE3) and purified using nickel affinity chromatography following the manufacturer's instruction. The purified QRS-N was then used to prepare polyclonal rabbit antibody as described previously [Park, 1999 #7366].

EXAMPLE 2

Cell Culture, Transfection, and Immunoprecipitation 293 and HeLa cells were grown in DMEM supplemented 10% fetal bovine serum (FBS), penicillin, and streptomycin. The cells were transfected with plasmid DNA by using Geneporter (GTS, San Diego, Calif.) according to manufacture's protocol. Twenty four hours after transfection, cells (100-mm dish) were washed twice in ice-cold phosphate-buffered saline (PBS) and lysed in 300 µl of IP-lysis buffer [50 mM Hepes (pH 7.4), 1% NP40, 150 mM NaCl, 10% glycerol, 1 mM EDTA] supplemented with 1 mM phenyl-methylsulfonyl fluoride and 5 µg/ml aprotinin. Extracts (1 mg of protein) were diluted in IP buffer (1 ml), and immunoprecipitated with 5 µg of antibody and 50 µl of a slurry of protein A-agarose beads (Sigma) for 3 hour at 4° C. The immunoprecipitates were washed three times with IP-lysis buffer, and boiled in Laemmli's loading buffer. Aliquots of cell lysates and immunoprecipitates resolved on SDS-PAGE were transferred to nitrocellulose membranes and probed with antibodies as specified, followed by secondary antibody conjugated with horseradish peroxidase (Pierce). After washing, proteins were detected by enhanced chemiluminescence (Amersham).

EXAMPLE 3

In Vitro Kinase Assay

Cells (100-mm dish) were transfected with plasmid DNA. Twenty four hours after transfection, cells were lysed with a buffer solution containing 20 mM Tris-HCl (pH 7.5), 12 β-glycerophosphate, 150 mM NaCl, 5 mM EGTA, 10 mM NaF, 1% Triton X-100, 0.5% deoxycholate, 3 mM DTT, 1 mM sodium orthovanadate, 1 mM PMSF, and 5 µg/ml aprotinin). The lysates (1 mg) were immunoprecipitated with antibody (5 µg) and 50 µl of protein A-agarose for 4 hours. The beads were washed twice with a solution containing 150 mM NaCl, 20 mM Tris-HCl (pH7.5), 5 mM EGTA, 2 mM DTT and 1 mM PMSF and once with a reaction buffer containing 20 mM Tris-HCI (pH 7.5) and 20 mM $MgCl_2$. MBP (40 µg/ml) or GST-SEK1 (20 µg/ml) was incubated with the immunoprecipitates in a reaction buffer containing 20 mM Tris-HCl (pH 7.5), 20 mM $MgCl_2$ and 0.5 µCi of [2-32P] ATP for 10 min at 30° C. Samples were analyzed by SDS-PAGE with an autoradiography.

EXAMPLE 4

Cell Death Assay

Cells were plated onto 6-well dishes the day before transfection for HeLa cells. The cells were by Geneporter (GTS) according to manufacturer's protocol. Twenty four hours after transfection, X-gal staining was done for 4 hours to overnight according to manufacturer's protocol (Invitrogen). The percentage of apoptotic cells was determined by the number of blue cells with apoptotic morphology divided by the total number of blue cells. Specific apoptosis was calculated as the percentage of blue cells with apoptotic morphology in each experimental condition minus the percentage of blue cells with apoptotic morphology in empty vector-transfected cells. At least 500 cells from three random fields were counted in each experiment, and the data shown are the average and SD of at least three independent experiment.

EXAMPLE 5

Construction of QRS Deletion Mutants

To make B42-Daxx full clone, PCR was carried out with a set of primers [forward:5'-CCGGAATTCCGGATGGCCACCGCTAACAGC(SEQ ID NO. 1) and backward: 5'-CCGCTCGAGCGGCTAATCAGAGTCTGAGAGC (SEQ ID NO. 2)] using Prk5-Flag-Daxx (a kind gift from Dr. X. Yang) as a template and the product was cloned into pGEX4T-1. B42-Daxx was constructed by insertion of the PCR product which was digested out by EcoRI and XhoI from pGEX-Daxx. B42-Daxx-C was a clone (encoding Daxx G604-D740) isolated from screening of yeast two hybrid using LexA-QRS-N as a bait.

To make LexA-QRS full clone, the QRS full gene was cut out from pGEX4T-1-QRS by EcoRI and NotI, and ligated into pEG202, a LexA vector. The plasmid, pGEX4T-1-QRS was made by the insertion of the QRS full gene from pM191 (a kind gift from Dr. K. Shiba) into pGEX4T-1 using XhoI and NotI sites. To make QRS-C clone, PCR was carried out with a set of primers [forward:5'- CCGCTCGAGATGAAC-TACAAGACCCCAGGCT (SEQ ID NO. 3) and backward: 5'- ATTTGCGGCCGCTCTAGAACTAGT (SEQ ID NO. 4)] using pM191 as a template and the product encoding from N237 to the C-terminal end, V775 of QRS was cloned into pGEX4T-1. LexA-QRS-C was constructed by insertion of the PCR product digested with EcoRI and NotI from pGEX-QRS-C.

To make QRS-N clone, PCR was carried out with a set of primers [forward: 5'-AATGAATTCATGGCGGCTCTAGACTCC (SEQ ID NO. 5) and backward: 5'-CCGGTCGACTCACTCACCAGGCTTGTGGAA (SEQ ID NO. 6)] using pM191 as a template and the product encoding from the N-terminus to E236 of QRS was cloned into pGEX4T-1. LexA-QRS-C was constructed by insertion of the PCR digested with EcoRI and NotI from pGEX-QRS-C into pEG202.

REFERENCES

1. K. Shiba, H. Motegi, P. Schimmel, *Trends Biochem. Sci.* 22, 453 (1997).
2. M. Mirande, *Prog. Nucleic Acid Res. Mol. Biol.* 40, 95 (1991).
3. L. L. Kisselev and A. D. Wolfson, *Prog. Nucleic Acid Res. Mol. Biol*, 48, 83 (1994).
4. D. C. H. Yang, in *Current Topics in Cellular Regulation*, 34, pp. 101–136 (1996).
5. K. Wakasugi and P. Schimmel, *Science* 284, 147 (1999).
6. S. G. Park, K. H. Jung, J. S. Lee, Y. J. Jo, H. Motegi, S. Kim, K. Shiba, *J. Biol. Chem.* 274, 16673 (1999).
7. U. E. Knies, H. A. Behrensdorf, C. A. Mitchell, U. Deutsch, W. Risau, H. C. A.
8. S. B. Rho et al., *Proc, Natl. Acad. Sci, USA*, 96, 4488 (1999).
9. J. Gyuris, E. Golemis, H. Chertkov, R. Brent, *Cell*, 75, 791 (1993).
10. X. Yang, R. Khosravi-Far, H. Y. Chang, D. Baltimore, *Cell*, 89, 1067 (1997).
11. H. Y. Chang, H. Nishitoh, X. Yang, H. Ichijo, D. Baltimore, *Science*, 281, 1860 (1998).
12. H. Ichijo et al., *Science*, 275, 90 (1997).
13. M. Saitoh, H. Nishitoh, F. Makijo, K. Takeda, K. Tobiume, Y. Sawada, M. Kawabata, K. Miyazono, H. Ichijo, *EMBO J*. 17, 2596 (1998).
14. A. D. Hollenbach, J. E. Sublett, C. J. Mcpherson, G. Grosveld, *EMBO J*. 18, 3702 (1999).
15. A. F. Pluta, W. C. Earnshaw, I. G. Goldberg, *J. Cell Sci*. 111, 2029 (1998).
16. S. B. Rho et al., *J. Biol. Chem.* 273, 11267 (1998).

What is claimed is:

1. A method for regulating apoptosis by a cell, comprising introducing into said cell a human glutaminyl-tRNA synthetase (QRS), wherein said synthetase consists essentially of a N-terminal extension domain and a C-terminal catalytic domain and wherein regulation of apoptosis is effected by interaction of said human glutaminyl-tRNA synthetase with a pro-apoptotic mediator and apoptosis signal-regulating kinase in said cell.

2. The method according to claim 1, wherein said N-terminal extension domain interacts with Daxx, thereby effecting inhibitory regulation.

3. The method of claim 1, said C-terminal catalytic domain interacts with ASK1, thereby effecting inhibitory regulation.

4. The method of claim 1, wherein said C-terminal catalytic domain blocks interaction between Daxx and ASK1, thereby effecting inhibitory regulation.

* * * * *